(12) United States Patent
Gonnelli

(10) Patent No.: US 9,814,831 B2
(45) Date of Patent: Nov. 14, 2017

(54) MOVING BASAL ENGINE FOR A FLUID DELIVERY DEVICE

(71) Applicant: Valeritas, Inc., Bridgewater, NJ (US)

(72) Inventor: Robert R. Gonnelli, Mahwah, NJ (US)

(73) Assignee: VALERITAS, INC., Bridgewater, NJ (US)

( * ) Notice: Subject to any disclaimer, the term of this patent is extended or adjusted under 35 U.S.C. 154(b) by 0 days.

(21) Appl. No.: 15/106,853

(22) PCT Filed: Jan. 28, 2015

(86) PCT No.: PCT/US2015/013283
§ 371 (c)(1),
(2) Date: Jun. 21, 2016

(87) PCT Pub. No.: WO2015/116677
PCT Pub. Date: Aug. 6, 2015

(65) Prior Publication Data
US 2017/0000942 A1    Jan. 5, 2017

Related U.S. Application Data

(60) Provisional application No. 61/934,259, filed on Jan. 31, 2014.

(51) Int. Cl.
*A61M 5/145* (2006.01)
*A61M 5/315* (2006.01)
(Continued)

(52) U.S. Cl.
CPC ........ *A61M 5/1454* (2013.01); *A61M 5/1452* (2013.01); *A61M 5/14248* (2013.01);
(Continued)

(58) Field of Classification Search
CPC ............ A61M 5/1424; A61M 5/14244; A61M 5/14248; A61M 5/145; A61M 5/1452;
(Continued)

(56) References Cited

U.S. PATENT DOCUMENTS 4,437,859 A    3/1984 Whitehouse et al.
4,561,856 A *  12/1985 Cochran ............... A61M 5/155
                                                     604/143

(Continued)

OTHER PUBLICATIONS

International Search Report and Written Opinion of ISA, dated May 6, 2015 for International Patent Application No. PCT/US15/13283.

*Primary Examiner* — Imani Hayman
*Assistant Examiner* — James D Ponton
(74) *Attorney, Agent, or Firm* — Morgan, Lewis & Bockius LLP

(57) ABSTRACT

A fluid delivery device comprises a fluid reservoir for containing medicament. The fluid reservoir is sealed proximate one end with a sliding seal piston. A delivery path is configured to fluidly couple the fluid reservoir and a patient wearing the fluid delivery device. A basal engine mechanism is configured to directly or indirectly move the sliding seal piston in the fluid reservoir at a controlled basal rate. A bolus mechanism configured to move the basal engine relative to the fluid reservoir and directly or indirectly move the sliding seal piston in the fluid reservoir a discrete bolus amount at a time.

15 Claims, 5 Drawing Sheets

(51) Int. Cl.
*A61M 5/14* (2006.01)
*A61M 5/142* (2006.01)

(52) U.S. Cl.
CPC ...... *A61M 5/14526* (2013.01); *A61M 5/3159* (2013.01); *A61M 5/31526* (2013.01); *A61M 5/31533* (2013.01); *A61M 5/31578* (2013.01); *A61M 5/14244* (2013.01); *A61M 2005/1405* (2013.01); *A61M 2005/14204* (2013.01); *A61M 2005/14506* (2013.01); *A61M 2005/14513* (2013.01)

(58) Field of Classification Search
CPC ............ A61M 5/14526; A61M 5/1454; A61M 5/16804; A61M 5/16877; A61M 2005/14506; A61M 2005/14513; A61M 5/315; A61M 5/31511; A61M 5/31525; A61M 5/31526; A61M 5/31533; A61M 5/31545; A61M 5/31546; A61M 5/31548; A61M 5/31555; A61M 5/31565; A61M 5/31576; A61M 5/31578; A61M 5/31593; A61M 5/31595

See application file for complete search history.

(56) References Cited

U.S. PATENT DOCUMENTS

| | | | |
|---|---|---|---|
| 4,568,335 A | 2/1986 | Updike et al. | |
| 7,632,245 B1* | 12/2009 | Cowan | A61M 5/14526 600/420 |
| 2005/0273059 A1* | 12/2005 | Mernoe | A61M 5/14248 604/180 |
| 2009/0028824 A1* | 1/2009 | Chiang | A61M 5/14248 424/85.7 |
| 2009/0240232 A1* | 9/2009 | Gonnelli | A61M 5/14526 604/506 |
| 2010/0063446 A1 | 3/2010 | Rush et al. | |
| 2013/0046239 A1 | 2/2013 | Gonnelli et al. | |

* cited by examiner

MOVING BASAL ENGINE FOR A FLUID DELIVERY DEVICE

CROSS-REFERENCE TO RELATED APPLICATIONS

This application is a U.S. National Stage filing of International Patent Application No. PCT/US15/13283 filed Jan. 28, 2015, which claims the benefit of U.S. Provisional Patent Application No. 61/934,259 filed Jan. 31, 2014 entitled "Moving Basal Engine For A Fluid Delivery Device", both of which are incorporated by reference herein in their entirety.

BACKGROUND OF THE INVENTION

The present invention generally relates to moving basal engine for a fluid delivery device.

BRIEF SUMMARY OF THE INVENTION

In one embodiment there is a fluid delivery device comprising: a fluid reservoir for containing medicament, the fluid reservoir being sealed proximate one end with a sliding seal piston; a delivery path configured to fluidly couple the fluid reservoir and a patient wearing the fluid delivery device; a basal engine mechanism configured to directly or indirectly move the sliding seal piston in the fluid reservoir at a controlled basal rate; and a bolus mechanism configured to move the basal engine relative to the fluid reservoir and directly or indirectly move the sliding seal piston in the fluid reservoir a discrete bolus amount at a time.

In one embodiment, the basal engine is contained within the bolus mechanism. In one embodiment, the basal engine includes a reservoir containing a hydraulic fluid under pressure from a stored energy source, the reservoir including an aperture configured to release the hydraulic fluid at a rate determined by the force of the stored energy source, the viscosity of the hydraulic fluid and the geometry of the aperture. In one embodiment, the hydraulic fluid that is released by the reservoir presses on the sliding seal piston. In one embodiment, the stored energy source includes one or more springs. In one embodiment, the stored energy source includes a compressed gas or a combustible material to create a compressed gas.

In one embodiment, the basal engine mechanism is an electrochemical device that expands in at least one dimension while being charged or discharged. In one embodiment, the electrochemical device is connected to a circuit to control the charge or discharge rate. In one embodiment, the electrochemical device is connected to a circuit for user interface and device function, wherein the circuit is powered by the discharge of the electrochemical device.

In one embodiment, the bolus mechanism slides within the fluid reservoir. In one embodiment, there is a hydraulic fluid between the basal engine mechanism and the sliding seal piston. In one embodiment, the sliding seal piston is in contact with the basal engine mechanism and the medicament. In one embodiment, the basal engine mechanism includes the sliding seal piston. In one embodiment, the basal engine mechanism includes a sliding seal, the sliding seal being in contact with a hydraulic fluid that is in contact with the sliding seal piston. In one embodiment, the fluid reservoir is contained within a housing having an adhesive patch configured to be adhered to a skin surface of a patient. In one embodiment, the delivery path includes a needle.

BRIEF DESCRIPTION OF THE SEVERAL VIEWS OF THE DRAWINGS

The following detailed description of embodiments of the moving basal engine for a fluid delivery device will be better understood when read in conjunction with the appended drawings of exemplary embodiments. These drawings focus on the fluid delivery system. It is to be understood that at least some of the figures and descriptions of the invention have been simplified to focus on elements that are relevant for a clear understanding of the invention, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein. For example, other portions of a final device are not shown in the drawings such as a mount, case or cover, needle or cannula deployment system, triggers for needle deployment, keys for activating or storing the system, skin attachment and other components to support the medicament delivery in a product. Portions of the fluid delivery devices disclosed in U.S. Patent Application Publication No. 2013/0046239, U.S. Patent Application Publication No. 2011/0306929, and U.S. Pat. No. 7,481,792 may be used in conjunction with the present invention and are hereby incorporated by reference in their entirety.

It should be understood, however, that the invention is not limited to the precise arrangements and instrumentalities shown.

In the drawings:

FIG. 1A is side view of a moving basal drive device in accordance with an exemplary embodiment of the present invention;

FIG. 1B is a perspective view of the moving basal drive device shown in FIG. 1A;

FIG. 1C is a cross sectional side view of the moving basal drive device shown in FIG. 1A;

FIG. 1D is a cross sectional side view of the moving basal drive device shown in FIG. 1A after some basal delivery;

FIG. 1E is a cross sectional side view of the moving basal drive device shown in FIG. 1A after some basal delivery and some bolus delivery;

FIG. 2A is a cross sectional side view of a moving basal drive device in accordance with an exemplary embodiment of the present invention;

FIG. 2B is a cross sectional side view of the moving basal drive device shown in FIG. 2A after some basal delivery;

FIG. 2C is a cross sectional side view of the moving basal drive device shown in FIG. 2A after some basal delivery and some bolus delivery;

FIG. 3A is a cross sectional side view of a moving basal drive device in accordance with an exemplary embodiment of the present invention after some basal delivery;

FIG. 3B is a cross sectional side view of the moving basal drive device shown in FIG. 3A after some basal delivery and some bolus delivery;

FIG. 4A is a cross sectional side view of a moving basal drive device having a limit controlled drive in accordance with an exemplary embodiment of the present invention;

Figure 4A:
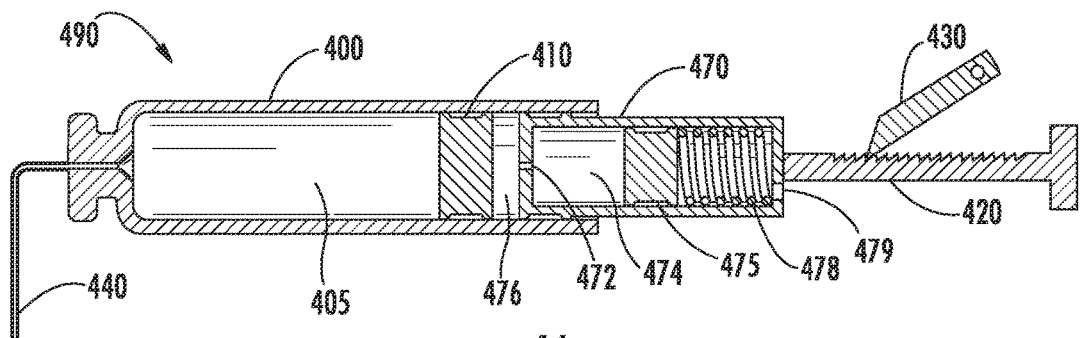
Figure 4B:
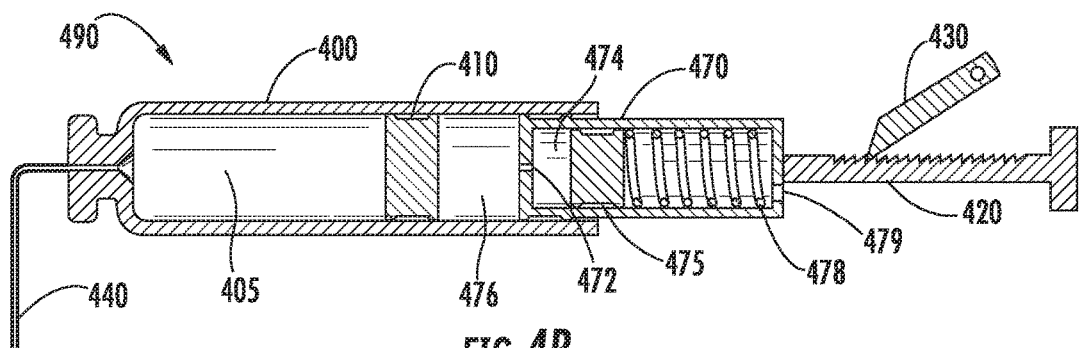
Figure 4C:
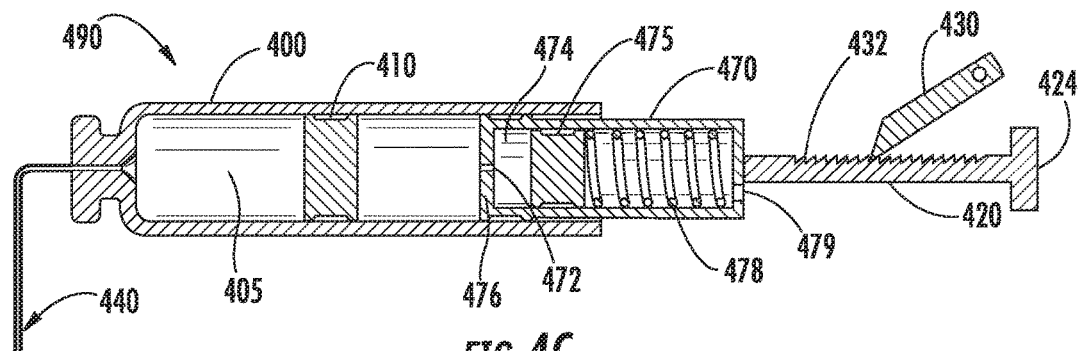

FIG. 4B is a cross sectional side view of the moving basal drive device shown in FIG. 4A after some basal delivery; and FIG. 4C is a cross sectional side view of the moving basal drive device shown in FIG. 4A after some basal and some bolus delivery.

DETAILED DESCRIPTION OF THE INVENTION

Portable systems for the delivery of basal and bolus doses of a medicament have been marketed for a number of years. Electronically driven medicament pumps are common and can be programmed to supply a steady low rate dose (i.e., basal) and controlled to supply higher doses on demand of the user (i.e., bolus). Wearable versions of insulin pumps for type I diabetes are marketed by a number of companies. In the last decade, wearable patch pumps that are adhered to the skin that can supply basal and bolus delivery have become available. These electronic pumps are quite complicated to use and very expensive and so have been mostly limited to patients who are critically dependent on at least daily drug delivery, such as type I diabetes.

More recently, great benefit of basal/bolus therapy has been found for type II diabetics. To address this need in a simpler and cheaper form, disposable non-electronic drive pumps have been developed where simpler and cheaper sources of stored energy, such as springs, have been utilized. While significantly cheaper, these devices are still difficult to make as compact and efficient as desired. Due to the drastic differences in supply rate, designs have resorted to separate drive systems for the basal and bolus supplies. This can increase the size of a device as well as increase the complexity.

Referring to FIGS. 1A-4C, four exemplary fluid delivery systems 190, 290, 390 and 490 for a fluid delivery device are shown. In one embodiment, the fluid delivery device is a discrete ambulatory medicament delivery pump. The fluid delivery devices may be single use, disposable and incapable of reuse. The fluid delivery devices may provide therapeutic capability in a small, single use, disposable package and can be produced using high volume manufacturing fabrication (e.g., injection molding) and assembly processes, allowing for low cost-of goods. Embodiments of the invention can be used for a broad range of applications, including, but not limited to, clinical applications (administration of medicaments, etc.) and biomedical research (e.g., microinjection into cells, nuclear or organelle transplantation, isolation of single cells or hybridomas, etc.).

In one embodiment, the fluid delivery devices are devices for dispensing, delivering, or administering the fluid or agent to the user or patient. The fluid may be a low viscosity gel agent and or a therapeutic agent. In one embodiment, the fluid is an analgesic agent. In one embodiment, the fluid is insulin. In one embodiment, the fluid is a U100 insulin. In another embodiment the fluid is a U200 insulin. In another embodiment the fluid is a U300 insulin. In another embodiment, the fluid is a U500 insulin. In another embodiment the fluid is any insulin concentration. In another embodiment the fluid is glucagon-like peptide-1 (GLP-1). In other embodiments, the fluid may be, but is not limited to, opiates and/or other palliatives or analgesics, hormones, psychotropic therapeutic compositions, or any other drug or chemical whose continuous dosing is desirable or efficacious for use in treating patients. Single fluids and combinations of two or more fluids (admixed or co-administered) may be delivered using the fluid delivery device. As used herein "patients" or "user" can be human or non-human animals; the use of the fluid delivery device is not confined solely to human medicine, but can be equally applied to veterinarian medicine.

The fluid delivery devices may dispense the fluid over a sustained period of time (i.e., basal delivery). In one embodiment, the fluid delivery rate is continuously or near continuously delivered to the user over the sustained period of time. The fluid delivery devices may also be capable of dispensing a supplementary amount of fluid, in addition to the basal amount, on demand, under patient control (i.e., bolus delivery). In one embodiment, the bolus amount delivered in a single, selectable administration is pre-determined.

In preferred embodiments, the fluid delivery device is partially electrochemically actuated (such as described in U.S. Patent Application Publication No. 2009/0028824 which is hereby incorporated by reference in its entirety) and comprises one or more reservoirs or chambers containing medicament fluid that is forced out of the device by either the electrochemical element expansion or a user moving the electrochemical element.

In preferred embodiments, the fluid delivery device is partially electrochemically actuated and comprises one or more reservoirs or chambers containing hydraulic fluid of a suitable viscosity for transferring power to the medicament fluid to force it out of the device by either the electrochemical element expansion or a user moving the electrochemical element.

In preferred embodiments, the fluid delivery devices are hydraulically actuated and comprises one or more reservoirs or chambers containing hydraulic fluid of a suitable viscosity for transferring power from one or more sources of stored energy to the medicament fluid wherein the delivery rate of the hydraulic fluid from the stored source of energy is controlled through restricted fluid flow and the source of restricted fluid flow can be moved by the user to provide additional medicament flow.

Referring to FIGS. 1A-1E, a first exemplary embodiment of a fluid delivery system 190 of a fluid delivery device is shown. A vial or reservoir 100 may contain a fluid 105 such as a medicament that may be delivered through a delivery path 140 (including e.g., a cannula, infusion set, or needle) at its distal end. In one embodiment, the fluid 105 is pushed out of the reservoir 100 through the needle 140 by the motion of a piston 110 that creates a movable seal with the wall of the reservoir 100. The motion of the piston 110 may be created or actuated in two ways. For basal rate motion and delivery, the piston 110 may be moved by the expansion of basal engine element 150 in the distal direction (i.e., toward the needle 140) and for bolus motion or delivery, the piston 110 may be moved by the distal motion of the entire basal engine.

In one embodiment, the basal engine element 150 is an electrochemical structure that expands as it discharges electricity through one or more leads 155. In one embodiment, the electrical output of the leads 155 is connected to a circuit that controls the current flow from the electrochemical basal engine element 150 establishing the expansion rate and thus the basal flow rate. In other embodiments, basal engine element 150 expands through the use of a gas, combustible material, liquid, foam and/or spring.

In one embodiment, as basal engine element 150 expands, it presses against the piston 110 and plunger 120. In one embodiment, the motion of plunger 120 is limited by the engagement of features 122 on plunger 120 and a pawl 130, having an end 132, that prevents the backward or proximal motion of the plunger 120. For bolus delivery, in one embodiment, the user depresses the proximal end 124 of plunger 120 in the distal direction forcing the plunger 120, the basal engine element 150 and the piston 110 in the distal direction forcing the bolus amount out essentially as quickly as the distal end 124 of the plunger 120 is depressed. In one embodiment, the application of force from the user to the distal end 124 of the plunger 120 is indirectly applied through a mechanism that limits its distal travel. In one embodiment, the distance that the plunger 120 can be depressed in one application of force is limited. In one embodiment, the distance the plunger 120 can be depressed is limited each time a release element is actuated. In one embodiment, the user presses on the pawl element 130 which transfers the force and motion to the plunger element 120 and the pawl element travel is limited on each push to limit the bolus delivery volume.

Figure 1A:
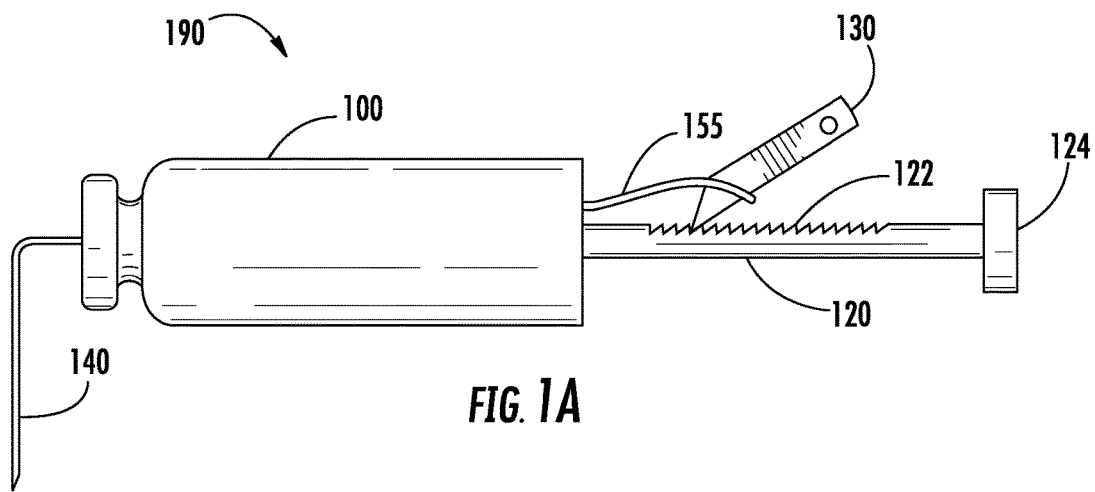
Figure 1B:
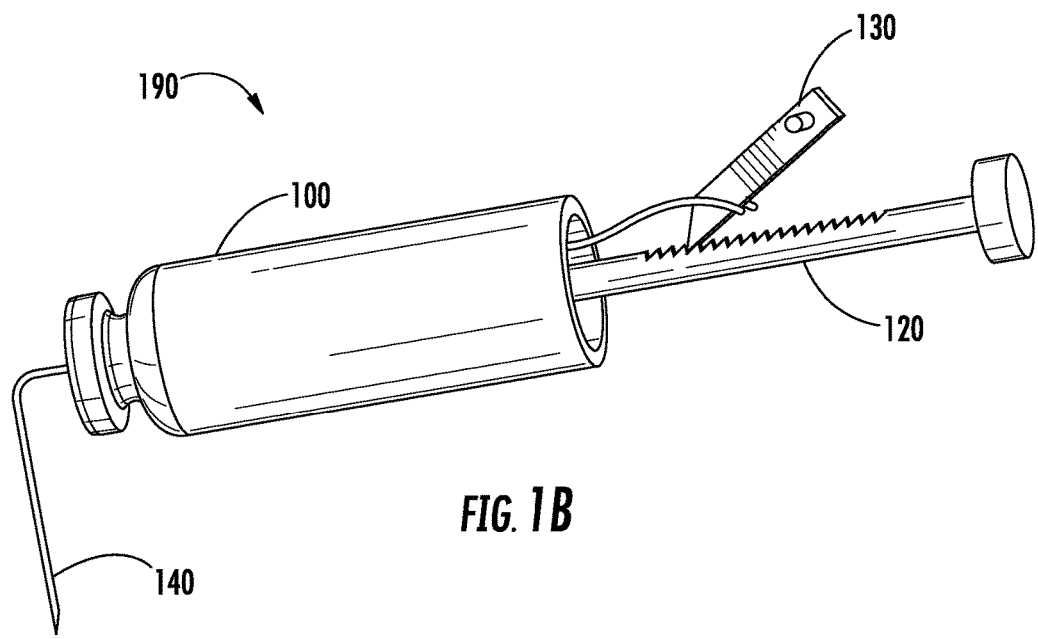
Figure 1C:
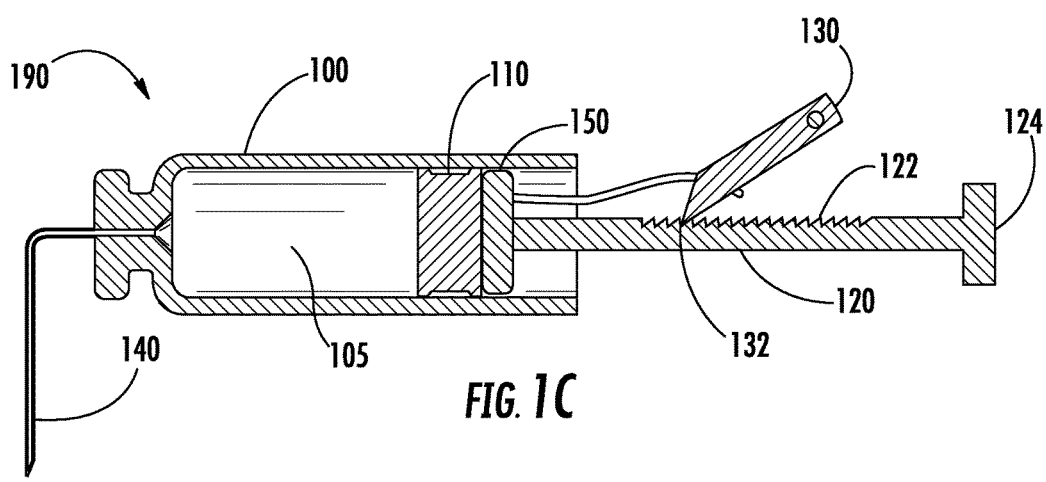

FIG. 1C shows the cross section of the fluid delivery system 190 of the fluid delivery device prior to any basal delivery. In this configuration, the plunger 120 has been depressed several bolus steps so the basal engine element 150 and piston 110 have moved distally forcing a number of bolus doses of medicament 105 out of the reservoir 100 through the needle 140 and into the patient.

Figure 1D:
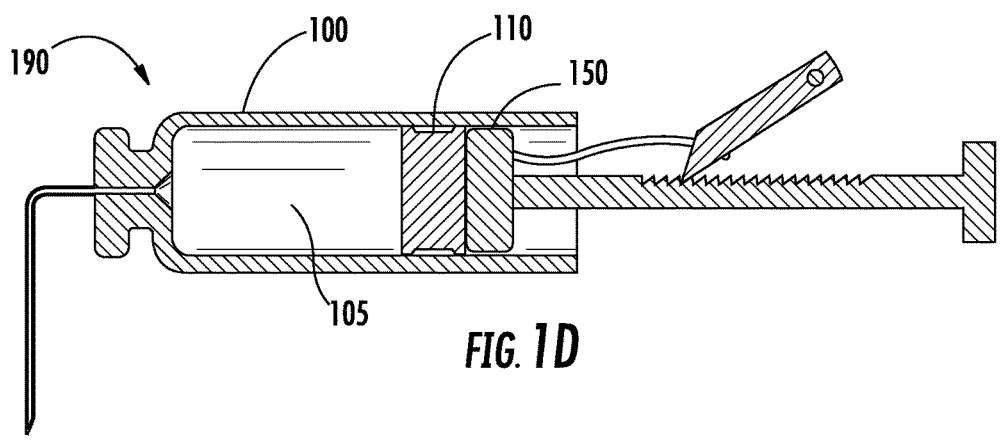

FIG. 1D shows the fluid delivery system 190 of the fluid delivery device after a period of time with the basal engine element 150 partially expanded. In this configuration, the expansion of the basal engine element 150 has forced the piston 110 in the distal direction as the plunger 120 prevents the basal engine element 150 from expanding in the proximal direction.

Figure 1E:
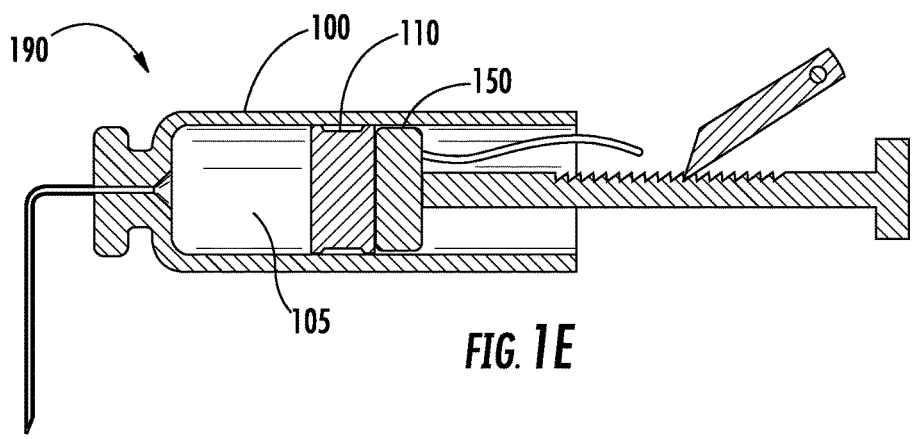

FIG. 1E shows the cross section of the fluid delivery system 190 of the fluid delivery device after basal delivery and additional bolus delivery have been delivered. In this configuration, the plunger 120 has been depressed several additional steps so the basal engine element 150 and the piston 110 have moved forcing more bolus doses of medicament 105 out of the reservoir 100 through the needle 140 and into the patient.

Figure 2A:
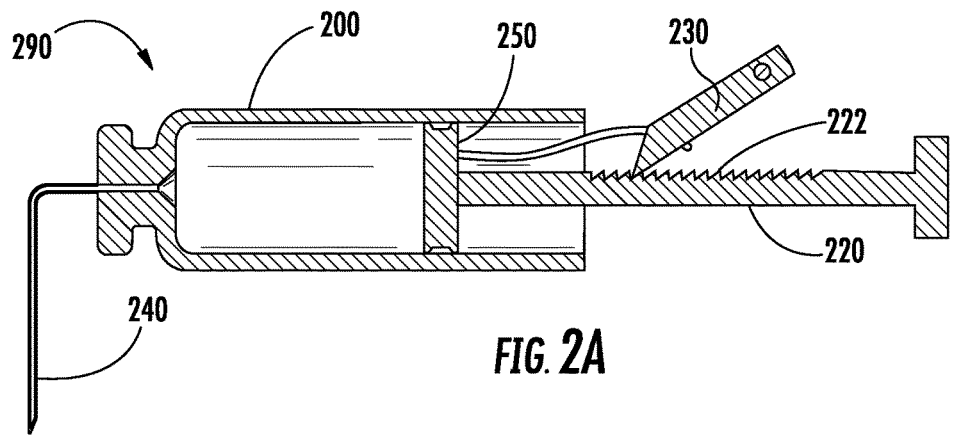
Figure 2B:
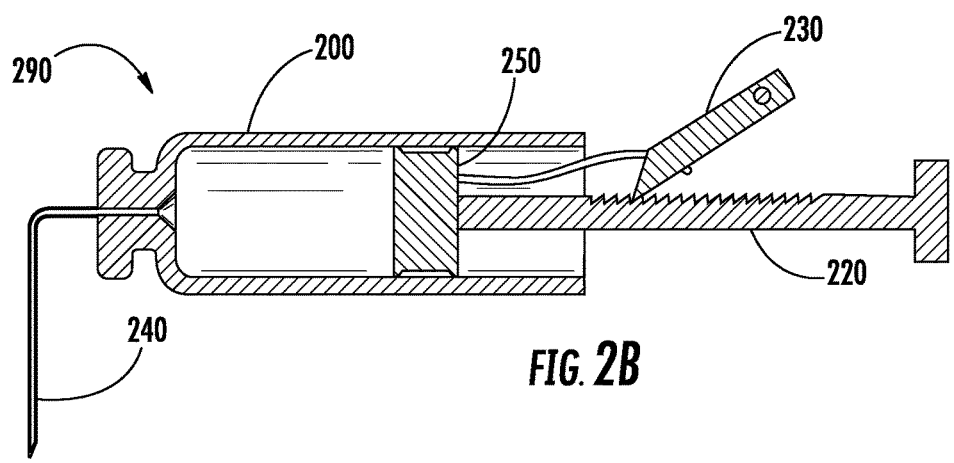
Figure 2C:
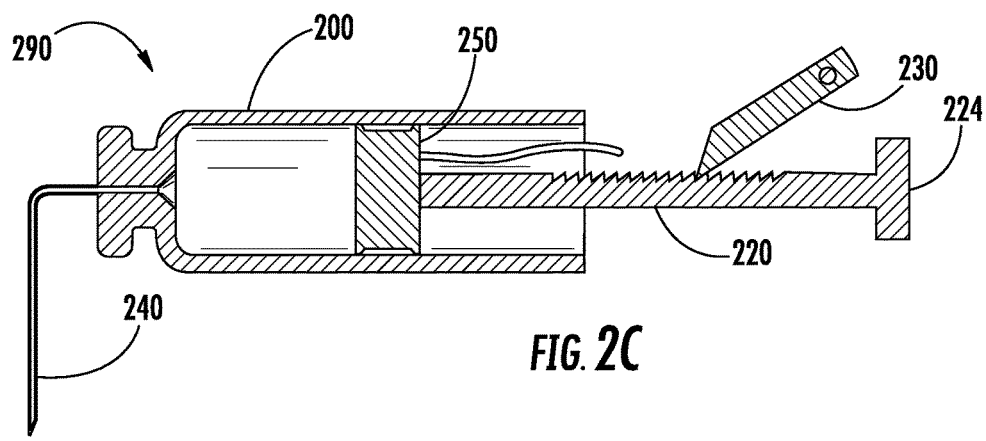

Referring to FIGS. 2A-2C, a second exemplary embodiment of the fluid delivery system 290 is shown. The fluid delivery system 290 is similar to the fluid delivery system 190 above except that basal engine element 250 forms the sliding seal and a separate sliding seal piston is omitted.

Figure 3A:
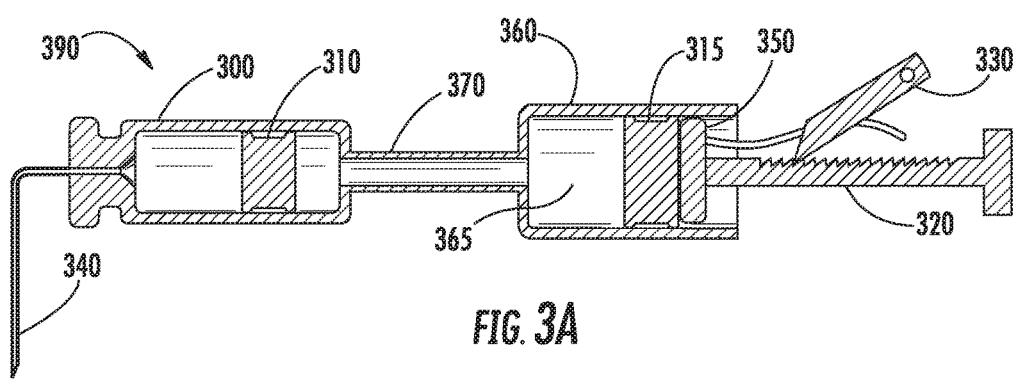
Figure 3B:
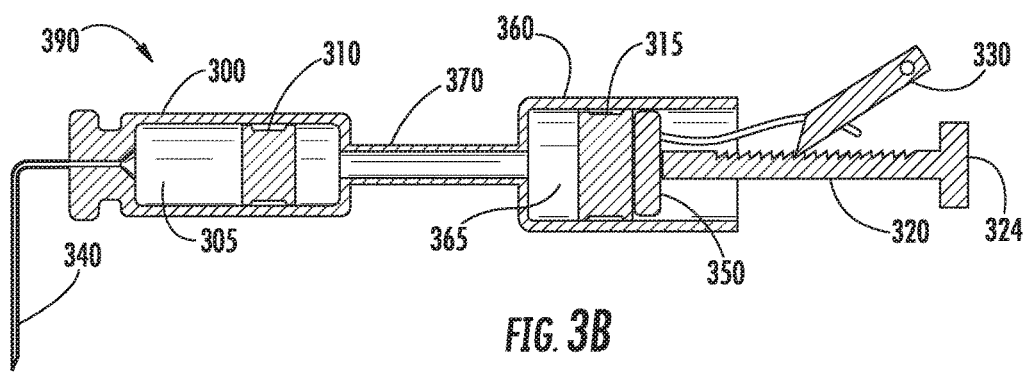

Referring to FIGS. 3A-3B, a third exemplary embodiment of the fluid delivery system 390 is shown. The fluid delivery system 390 is similar to the fluid delivery system 190 above except that a sliding seal element 315 is provided and there is a fluid passage 370 between the sliding seal piston 310 and the sliding seal element 315. In one embodiment, moving the plunger 320 and the basal engine element 350 in the distal direction forces the hydraulic fluid 365 to flow out of the hydraulic reservoir 360 through the passage 370 moving the sliding seal piston 310.

In one embodiment, the passage 370 for the hydraulic fluid between the sliding seal piston 310 and the sliding seal element 315 (such as a second piston or a sliding seal on the basal engine element 350) is not straight. For example, the passage 370 may be U-shaped such that the basal engine is generally parallel with the reservoir 300 to reduce the length of the device and allow for a more compact system. In one embodiment, the passage 370 for the hydraulic fluid 370 is not of constant shape or cross sectional area to make molding and fabrication of the fluid channel simpler.

Referring to FIGS. 4A-4C, a fourth exemplary embodiment of the fluid delivery system 490 is shown. The fluid delivery system 490 is similar to the fluid delivery system 190 above except that the basal engine 470 is configured to slide within the reservoir 400 while creating a seal between the basal engine 470 and the reservoir 400. In one embodiment, the reservoir 400 is configured such that the piston 410 is in contact with the medicament 405 and is not the same part, size or shape as the reservoir that the basal engine 470 can slide within, but the reservoirs are fluidly connected to one another.

The motion of the hydraulic fluid in space 476 that acts to move the sliding seal piston 410 may be created in two ways. For basal delivery, the hydraulic fluid within a hydraulic fluid reservoir 474 moves from within the basal engine 470 into a space 476 proximal to the first piston 410 forcing the first piston 410 in the distal direction. A basal engine includes the hydraulic fluid reservoir 474 that is pressurized by a second sliding seal piston 475 under the force of a stored energy source 478 such as a compressed elastic element. The hydraulic fluid reservoir 474 includes a specifically sized flow restriction opening 472 that is configured to release the pressurized hydraulic fluid at a basal rate into the space 476 between the basal engine 470 and the first piston 410. The size of the aperture 472, the pressure from the energy source 478, the viscosity of the hydraulic fluid and the friction of the sliding piston 475 may determine the flow rate out of the basal engine 470 and thus basal medicament delivery rate. In one embodiment, the stored energy source 478 includes one or more springs. In alternative embodiments, the compressed elastic element 478 includes a compressed gas and/or combustible material(s).

For bolus delivery, the entire basal engine 470 may be moved relative to the medicament reservoir 400 forcing the hydraulic fluid in the space 476 in the distal direction. In one embodiment, the passage for the hydraulic fluid through space 476 is not straight to allow a more compact configuration of the device. In one embodiment, the passage for the hydraulic fluid through space 476 is not of constant shape or cross sectional area to allow for easier molding and assembly.

It will be appreciated by those skilled in the art that changes could be made to the exemplary embodiments shown and described above without departing from the broad inventive concepts thereof. It is understood, therefore, that this invention is not limited to the exemplary embodiments shown and described, but it is intended to cover modifications within the spirit and scope of the present invention as defined by the claims. For example, specific features of the exemplary embodiments may or may not be part of the claimed invention and various features of the disclosed embodiments may be combined. Unless specifically set forth herein, the terms "a", "an" and "the" are not limited to one element but instead should be read as meaning "at least one".

Further, to the extent that the methods of the present invention do not rely on the particular order of steps set forth herein, the particular order of the steps should not be construed as limitation on the claims. Any claims directed to the methods of the present invention should not be limited to the performance of their steps in the order written, and one skilled in the art can readily appreciate that the steps may be varied and still remain within the spirit and scope of the present invention.

I claim:

1. A fluid delivery device comprising:
    a housing including a fluid reservoir for containing medicament, the fluid reservoir being sealed proximate one end with a sliding seal piston;
    a delivery path configured to fluidly couple the fluid reservoir and a patient wearing the fluid delivery device;
    a basal actuator slidingly coupled to an inside surface of the fluid reservoir and configured to directly or indirectly move the sliding seal piston in the fluid reservoir at a controlled basal rate; and
    a bolus actuator coupled to a proximal end of the basal actuator and configured to move the basal actuator relative to the fluid reservoir and move the sliding seal piston in the fluid reservoir a discrete bolus amount at a time, wherein the basal actuator is contained within the bolus actuator, and wherein the basal actuator includes a reservoir containing a hydraulic fluid under pressure from a stored energy source, the reservoir of the basal actuator including an aperture configured to release the hydraulic fluid at a rate determined by the force of the stored energy source, the viscosity of the hydraulic fluid and the geometry of the aperture.

2. The fluid delivery device of claim 1, wherein the hydraulic fluid that is released by the reservoir of the basal actuator presses on the sliding seal piston.

3. The fluid delivery device of claim 1, wherein the stored energy source includes one or more springs.

4. The fluid delivery device of claim 1, wherein the stored energy source includes a compressed gas or a combustible material to create a compressed gas.

5. The fluid delivery device of claim 1, wherein the basal actuator includes an electrochemical device that expands in at least one dimension while being charged or discharged.

6. The fluid delivery device of claim 5, wherein the electrochemical device is connected to a circuit to control the charge or discharge rate.

7. The fluid delivery device of claim 5, wherein the electrochemical device is connected to a circuit for user interface and device function, wherein the circuit is powered by the discharge of the electrochemical device.

8. The fluid delivery device of claim 1, wherein the sliding seal piston is in contact with the basal actuator and the medicament.

9. The fluid delivery device of claim 1, wherein the basal actuator includes the sliding seal piston.

10. The fluid delivery device of claim 1, wherein the basal actuator includes a sliding seal, the sliding seal being in contact with the hydraulic fluid that is in contact with the sliding seal piston.

11. The fluid delivery device of claim 1, wherein the housing includes an adhesive patch configured to be adhered to a skin surface of a patient.

12. The fluid delivery device of claim 1, wherein the delivery path includes a needle.

13. The fluid delivery device of claim 1, wherein the bolus actuator includes a plunger.

14. The fluid delivery device of claim 13, wherein the plunger includes a rack coupled to a pawl.

15. A method of using a fluid delivery device having a housing including a fluid reservoir configured to contain medicament, the fluid reservoir being sealed proximate one end with a sliding seal piston, a delivery path configured to fluidly couple the fluid reservoir and a patient wearing the fluid delivery device, a basal actuator within the housing and including an electrochemical device, and a bolus actuator coupled to a proximal end of the basal actuator, the method comprising the steps of:

expanding the electrochemical device by charging or discharging the electrochemical device to move the sliding seal piston in the fluid reservoir at a controlled basal rate; and selectively sliding the basal actuator relative to the fluid reservoir and the housing to move the sliding seal piston in the fluid reservoir a discrete bolus amount at a time.

* * * * *